United States Patent [19]

Kaneko et al.

[11] Patent Number: 5,272,072
[45] Date of Patent: Dec. 21, 1993

[54] METHOD FOR PREPARING TRANSFORMED PLANT

[75] Inventors: Takafumi Kaneko; Kazutoshi Ito, both of Nitta, Japan

[73] Assignee: Sapporo Breweries Limited, Tokyo, Japan

[21] Appl. No.: 784,709

[22] Filed: Oct. 30, 1991

[30] Foreign Application Priority Data

Nov. 1, 1990 [JP] Japan .................. 2-293582

[51] Int. Cl.$^5$ .............. C12N 15/12; C12N 5/00; A01H 1/04
[52] U.S. Cl. ................. 435/172.3; 800/205; 800/DIG. 55; 435/240.49; 435/240.5
[58] Field of Search ............ 800/205, DIG. 55; 435/172.3, 240.45, 240.5, 173, 240.49, 240.5; 935/52

[56] References Cited

U.S. PATENT DOCUMENTS

4,840,906 6/1989 Hunter et al. .................. 435/240.49

FOREIGN PATENT DOCUMENTS

| | | |
|---|---|---|
| 0270356 | 6/1988 | European Pat. Off. |
| 0275069 | 7/1988 | European Pat. Off. |
| 0290395 | 11/1988 | European Pat. Off. |
| 0334539 | 9/1989 | European Pat. Off. |
| WO89/00602 | 1/1989 | PCT Int'l Appl. |

OTHER PUBLICATIONS

Finn Lok Olsen, "Induction of Microspore Embryogenesis in Cultured Anthers of Hordeum Vulgare. The Effects of Ammonium Nitrate, Glutamine and Asparagine as Nitrogen Sources", Carlsberg Res. Commun., vol. 52, pp. 393-404 (1987).

K. J. Kasha et al., "Haploids in Cereal Improvement: Anther and Microspore Culture", Gene Manipulation in Plant Improvement II, Plenum Press, New York, pp. 213-235 (1990).

D. Clapham et al., "Haploid Hordeum Plants from Anthers in Vitro", Z. Pflanzenzuchtg, 69, pp. 142-155 (1973).

Michael W. Lassner et al., "Simultaneous Amplification of Multiple DNA Fragments by Polymerase Chain Reaction in the Analysis of Transgenic Plants and Their Progeny", Plant Molecular Biology Reporter, vol. 7(2), pp. 116-128 (1989).

A. Ziauddin et al., "Improved Plant Regeneration from Shed Microspore Culture in Barley (*Hordeum vulgare* L.) CV. Igri", Plant Cell Reports, vol. 9, pp. 69-72 (1990).

B. Foroughi-Wehr et al., "Plant Production from Cultured Anthers of *Hordeum vulgare* L.", Z. Pflanzenzuchtg., vol. 77, pp. 198-204 (1976).

Randall K. Saiki et al., "Primer-Directed Enzymatic Amplification of DNA with a Thermostable DNA Polymerase", Science, vol. 239, pp. 487-491 (Jan. 29, 1988).

Ingo Potrykus, "Gene Transfer to Cereals: An Assessment", Biotechnology, pp. 535-542 (Jun. 1990).

Weber, G., et al., Plant Cell, Tissue, and Organ Culture, vol. 12, (1988), pp. 219-222.

*Primary Examiner*—David T. Fox
*Assistant Examiner*—Charles Rories
*Attorney, Agent, or Firm*—Oblon, Spivak, McClelland, Maier & Neustadt

[57] ABSTRACT

A transformed plant of Gramineae is prepared by culturing an anther of Gramineae in a callus induction medium and, at a stage immediately before the microspore begins to cause division or during the initial division, transducing a genetic substance into the microspore cell through a pore formed by a laser pulse thereby to express genetic information of the genetic substance.

According to the present invention, it is unnecessary to prepare protoplast and therefore, time and operations for transformation can be greatly reduced. Since haploid cells are transformed, the character transduced is conveyed without separating at a later generation. In addition, difficulties in experiments between species and strains are minimized so that it is easy to apply the present invention to practical species. According to the present invention, large pores can be formed as compared to the electroporation method so that DNA or substances having a large molecular weight can be introduced.

8 Claims, No Drawings

METHOD FOR PREPARING TRANSFORMED PLANT

BACKGROUND OF THE INVENTION

1. Field of the Invention

The present invention relates to a method for preparing transformed plant of the family Gramineae and a method for transforming a plant of the family Gramineae.

2. Statement of the Prior Art

As a method for transforming a plant, genetic transduction utilizing Agrobacterium has been established. However, Agrobacterium fails to infect grasses of the family Gramineae and other techniques have been attempted.

As one of the techniques, direct transduction of vector DNA has been studied. For example, there is reported a method for transforming by means of electroporation, particle gun, polyethylene glycol or microinjection, that is, it is possible to transduce a gene into protoplast or callus in corns [Nature, 319, 791 (1986)], grasses [Mol. Gen. Genet., 204, 204 (1986)], wheat [Mol. Gen. Genet., 199, 178 (1985)]and pasture [Mol. Gen. Genet., 199, 178 (1985)]. In all of these methods, obtaining transgenic plant is greatly restricted by the difficulty of protoplast culture and the complicated handling. As an example where a gene is transduced to a plant, there is a report that plasmid is injected into young seedling rye by microinjection and the gene is expressed in seeds derived from the plant [Nature, 325, 274 (1986)]. However, this technique has not yet been established as a method for transducing a gene into a plant efficiently.

There is also reported a method for preparing a transformed plant using the transduction system in Gramineae by electroporation to protoplast [Japanese Patent Published Unexamined Application No. 1-18179]. In many of cereal plants, the regeneration from protoplast has not been established. In addition, many selection cultures and long periods of time are required for preparation of protoplast. It is also the actual situation that protoplast culture is applicable only to a part of the species and cultivars having excellent tissue culture property, even though they are the same crop.

A method for transformation by a laser perforation is currently utilized for transformation of an animal cell and used for preliminary experiments on plant tissues and cells [Weber et al., Plant Cell Tissue and Organ Culture, 12, 219 (1988)], and experiments on organelle [West German Patent Application 3,707,111A]. However, it is unknown to transform microspore of a plant by the method described above. There is also reported a method for preparing a transgenic plant using the gene transduction system into sweet corn embryo by a laser [Japanese Patent Published Unexamined Application No. 2-9378]. According to this method, however, the thus obtained transformant is a chimera. Any method for obtaining a transformant has not been established with respect to cereal plants.

As described above, many attempts have been made on transformation of a plant but transformation has not been yet successful for monocotyledons, especially in Gramineae, although it has been long desired.

SUMMARY OF THE INVENTION

As a result of extensive investigations in view of the foregoing problems, the present inventors have find a method for obtaining transgenic plants of the family Gramineae which comprises efficiently transducing a foreign gene into microspore of the plants belonging to the family Gramineae.

That is, the present invention provides a method for transforming Gramineae which comprises culturing an anther of Gramineae in a callus induction medium and, at a stage immediately before the enveloped microspore begins to cause division or during the initial division, transducing a genetic substance to the pollen cell through a pore formed by a laser pulse. The present invention also provides a method for obtaining transgenic plant which comprises expressing genetic information of the genetic substance in the transformant.

DETAILED DESCRIPTION OF THE PREFERRED EMBODIMENTS

Hereafter the present invention is described in detail.

The method of the present invention can generally be performed by culturing an anther in a callus induction medium and, suspending suitable microspores at a stage immediately before the single cells begin to cause division or during the initial division, in a solution, typically an aqueous solution, containing a genetic substance bearing genetic information to be transduced. Then, a laser device is focused on one of the microspore cells, the laser is excited to form pores in the cell emvelope. Through the pores, the genetic substance is introduced into the cell. The cell is cultured in callus induction medium to form callus and/or embryoid. The callus and/or embryoid are then subcultured on medium for regeneration. The transgenic plant can thus be obtained.

To culture appropriate microspore cells at such a stage immediately before the single cells begin to cause division or during the initial division by culturing the anther of Gramineae in callus induction medium, the anther is cultured in a medium chosen based on the property of anther to be cultured, from (1) modified MS medium [Carlsberg Res. Commun., 52, 393 (1987)], (2) FHG medium [Kasha et al., XIX Stadler Genetics Symp., 213 (1989)], (3) Clapham I, II, III medium [Z. Pflanzenzucht, 69, 142 (1973)], Foroughi-Weir et al. medium [Z. Pflanzenzucht, 77, 198 (1976)]listed hereunder, and modified media thereof.

| mg/ | 1) | 2) | 3)-I | 3)-II | 3)-III | 4) |
|---|---|---|---|---|---|---|
| Macroelements | | | | | | |
| $NH_4NO_3$ | 165 | 165 | 1650 | 1650 | 1650 | 1650 |
| $KNO_3$ | 1900 | 1900 | 1900 | 1900 | 1900 | 1900 |
| $CaCl_2.H_2O$ | 440 | 440 | 440 | 440 | 440 | 440 |
| $MgSO_4.7H_2O$ | 370 | 370 | 370 | 370 | 370 | 370 |
| $KH_2PO_4$ | 170 | 170 | 170 | 170 | 170 | 170 |
| $FeNa_2.EDTA$ | 40 | 40 | | | | 40 |
| $FeSO_4.7H_2O$ | | | 27.8 | 27.8 | 27.8 | |
| $Na_2EDTA$ | | | 37.3 | 37.3 | 37.3 | |
| Microelements | | | | | | |

-continued

| mg/ | 1) | 2) | 3)-I | 3)-II | 3)-III | 4) |
| --- | --- | --- | --- | --- | --- | --- |
| H₃BO₃ | 6.2 | 6.2 | 6.2 | 6.2 | 6.2 | 6.2 |
| MnSO₄.4H₂O | 22.3 | 22.3 | 22.3 | 22.3 | 22.3 | 22.3 |
| ZnSO₄.4H₂O | 8.6 | 8.6 | 8.6 | 8.6 | 8.6 | 8.6 |
| KI | 0.83 | 0.83 | 0.83 | 0.83 | 0.83 | 0.83 |
| Na₂MoO₄.2H₂O | 0.25 | 0.25 | 0.25 | 0.25 | 0.25 | 0.25 |
| CuSO₄.5H₂O | 0.025 | 0.025 | 0.025 | 0.025 | 0.025 | 0.025 |
| CoCl₂.6H₂O | | | 0.025 | 0.025 | 0.025 | |
| Organic elements | | | | | | |
| BAP | 1 | 1 | | 1 | | 1 |
| IAA | | | 0.2 | 1 | | 1 |
| TIBA | | | | | 0.02 | |
| Glutamine | 750 | 750 | | | | |
| alanin | | | | 400 | | |
| Myo-inositol | 100 | 100 | 100 | 100 | 100 | 100 |
| Thiamine HCl | 0.4 | 0.4 | 0.4 | 0.4 | 0.4 | 0.4 |
| Coconut milk | | | | 100000 | | |
| Sucrose | 60000 | | 120000 | 30000 | 120000 | 60000 |
| Maltose | | 62000 | | | | |
| Ficol 400 | 200000 | | | | | |
| Oxid Ionagar No. 2 | | | 7000 | 7000 | 7000 | 7000 |
| pH | 5.6 | 5.6 | 5.5 | 5.5 | 5.5 | 5.5 |

A temperature for the culture varies depending on the anther cultured but is generally in the range of 22° to 28° C., preferably at about 25° C. A time period for the culture varies depending upon the anther cultured but is generally in the range of 0 to 14 days. Laser treatment should be done when microspore cells acquires the ability to devide and replicate DNA in callus induction medium, that is, the microspore cells changes to cytoplasm-rich cells morphologically. Generally, the microspore changes to the cells proper for laser treatment within 2 weeks.

In addition, shed pollen cells obtained by the method of Ziauddin et al. [Plant Cell Reports, 9, 59 (1990)] may also be used.

The details of the method are described hereunder:

Donor plants. Seeds of barley (Hordeum vulgars L.) cv. Igri were germinated in turface at 20° C., 75% RH and a 16 h day (200 μE/m²/sec). After 7-10 days the seedlings were transferred to a vernalization cabinet at 4° C., 60% RH and a 8 h day (40 μE/m²/sec). After 8 weeks, the plants were transferred to 15 cm pots containing a 3:2:1 mixture of Guelph clay-loam, turface and peat moss and placed in a growth cabinet with 12° C. day/10° C. night for 16 h of Grow-lux fluorescent plus incandescent 50 W bulbs (100 μE/m²/sec). The plants were fertilized twice a week using water soluble 20-20-20 and 28-14-14, alternatively. The duration of the growth period was about 7 weeks. The spikes were harvested when the pollen was in the mid to late uninucleate stage (Wheatley et al, 1986).

Mechanically isolated microspore culture. The detailed protocol described by Hunter (1987, 1988), including the use of 28 day cold-pretreated spikes, was repeated. Subsequently, a modification to the technique found to be essential was the use of 0.3M mannitol rather than media for isolation and centrifugation of microspores.

REFERENCES

Wheatley W. G., Marsolais, A. A. and Kasha, K. J. Plant Cell Reports, 5, 47-49 (1986).

Hunter C. P. EP 0 245 892-A2, Plant generation method, pp. 1-8 (1987).

Hunter C. P. Ph.D. Thesis, Plant regeneration from microspores of barley, Hordeum vulgars; Wye College, University of London, (1988).

Examples of Gramineas used herein include sweet corns, cereal plants, etc. Specific examples of the cereal plants are barleys, wheats, ryes, oats, etc. Barleys include Dissa, Igri, TRUMPF, CARINA, Haruna Nijo, etc. The anther may be collected from these plants in a conventional manner.

The microspore cells used are isolated from the anther.

The genetic substance bearing genetic information is the one controlled to stabilize its genetic information and express the genetic information in Gramineae. A specific example of the genetic substance is a plasmid which functions in Gramineae. Examples of the promoter which functions in Gramineae are promoters derived from califlower mosaic virus such as CaMV35S, CaMV19S, etc.; PR protein promoter, ADH-1 promoter, etc.; terminators such as CaMV19S, NOS, etc. The genetic substance possesses, as the transformation properties, insect-resistant genes such as a deisred BT toxin, portease inhibitor, etc.; foreign gene such as virus-resistant gene, gene for storage protein such as cazein, glutenin, etc., transposable gene such as Ac, Da, etc. In addition, the genetic substance may contain a chemical-resistant such as herbicide-resistant gene, anti-biotics resistant gene and function as an initial selection marker.

The solution containing the genetic substance may contain about 10 to 20,000 μg/ml of the gene desired to be transduced into the cell and other components, specifically, inactivated salts for promoting equilibration of an accurate osmosis or high tension, cell nutrients or other additives. A more specific example is a gene suspension containing 9 to 15% of mannitol.

Next, the laser device is focused on one of the pollen cells and the laser is excited to form pores in the cell envelop. Through the pores, the genetic substance is introduced into the cells. A size of the pore may be varied but should not be excessively large, as compared to the size of the cell. Specifically, the pore having a diameter of generally 5 to 500 nm is formed. A time period for applying the pulse is generally in the range of 5 to 20 nanoseconds, preferably 10 to 15 nanoseconds.

The pulse energy is controlled generally in the range of 0.1 to 10 μJ. As the laser device, any optional device by which a laser can be focused on the appropriately fine focus may be generally used. Preferably, there may be used Hitachi Laser Cell Processor manufactured by Hitachi Ltd. which is commercially available as a device already utilized for laser microsurgery of mammal cells.

After the laser processing, the microspore cells are incubated in a solution containing the genetic substance for a time period sufficient to disperse and permeate the genetic substance from its solution into the cells with pores. A time period for the incubation is generally for 5 seconds to 2 hours and a temperature for the incubation is generally at 0° to 28° C.

After the laser processing and the incubation are carried out as described above, the resulting microspore cells or cells derived therefrom are cultured to form plants. A preferred embodiment of the present invention includes the method of Olsen et al. [Carlsberg Res. Commun., 52, 393 (1977)], the method of Ziauddin et al. [Plant Cell Reports, 9, 59 (1990)].

2.2. Methods 2.2.1 Donor plants

Seeds were germinated in a 1:1:2 soil mix, composed of K-soil (Sphagnum), Peat compost and Perlite, in 0.2 liter pots, at 20° C., 85% RH, and a 24 h day (40 μE·m$^2$·s$^{-1}$ Philips cold white). the light intensity is in all cases measured at the top of the pot or other culture containers.

After 5-6 days, when the plantlets had reached a height of about 5 cm the pots were transferred to a vernalization room (4° C., 85% RH and 10 h light, 105 μE·m$^2$·s$^{-1}$ Philips warm white). The pots were placed on a capillary mat in a pool of water which gave a continuous supply of water.

After eight weeks the plant were potted in 1.5 liter pots, in the same soil mixture as was used for germination and vernalization, and placed in a Conviron E8 growth chamber at 12°C., 70-80% Rh and 16 h light (120 μE·m$^2$·s$^{-1}$ Sylvania WHO/incandescent bulbs, 75%/25% on watt basis).

The duration of the growth period was approximately 7 weeks. Liquid fertilizer was applied 4 times a week according to the schedule (Table I) kindly provided by Dr. Hunter.

TABLE I

Nutrient supply for donor plants. Milliliters of liquid fertilizer (1:2 mixture of Chempack Numbers 1 and 2, (Chempack, Hoddesdon, Herts, UK) final concentration 6.75 g l$^{-1}$ (25:11:11 N:P:K) applied per 1.5 pot).

| Week | 0 | 1 | 2 | 3 | 4 | 5 | 6 | 7 |
|---|---|---|---|---|---|---|---|---|
| Day | | | | | | | | |
| 1 | — | 5 | 5 | 10 | 10 | 10 | 10 | 10 |
| 3 | — | — | — | 10 | 10 | 10 | 10 | 10 |
| 5 | — | — | 5 | 5 | 10 | 10 | 10 | 10 |
| 7 | — | — | — | — | 5 | 5 | 5 | 5 |

2.2.2. Tissue culture

The spikes were harvested when the pollen was in the mid uninucleate stage. Spikes at the desired developmental stage were preselected on the basis of the interligule length between the flag leaf and the second leaf, and on the thickness of the tiller.

TABLE II

Media for anther culture in Hordeum. Modified MS medium after FOROUGHI-WEHR et al. (Plant production from cultured anthers of *Hordeum vulgare* L. Z. Pflanzenzuchtg. 77, 198-204 (1976)). KAO and HORN (Induction of pollenplant formation in barley anther culture. International Symposium on Genetic Manipulation in Crops. October 22-26, Beijing, China (1984)) and HUNTER (The effect of anther orientation on the production of microspore-derived embryoids and plants of *Hordeum vulgare* cv. Sabarlis. Plant Cell Rep. 4, 267-268 (1985)).

| | I | II | III |
|---|---|---|---|
| Macroelements | mg l$^{-1}$ | mg l$^{-1}$ | mg l$^{-1}$ |
| NH$_4$NO$_3$ | 165 | 165 | 165 |
| KNO$_3$ | 1900 | 1900 | 1900 |
| CaCl$_2$.2H$_2$O | 440 | 440 | 440 |
| MgSO$_4$.7H$_2$O | 370 | 370 | 370 |
| KH$_2$PO$_4$ | 170 | 170 | 170 |
| FeNa$_2$EDTA | 40 | 40 | 40 |
| Microelements | | | |
| H$_3$BO$_3$ | 6.2 | 6.2 | 6.2 |
| MnSO$_4$.4H$_2$O | 22.3 | 22.3 | 22.3 |
| ZnSO$_4$.4H$_2$O | 8.6 | 8.6 | 8.6 |
| KI | 0.83 | 0.83 | 0.83 |
| Na$_2$MoO$_4$.2H$_2$O | 0.25 | 0.25 | 0.25 |
| CuSO$_4$.5H$_2$O | 0.025 | 0.025 | 0.025 |
| Organic elements | | | |
| BAP | 1 | 0.4 | — |
| Glutamine | 750 | 750 | 750 |
| Myo-inositol | 100 | 100 | 100 |
| Thiamine HCl | 0.4 | 0.4 | 0.4 |
| Sucrose | 60,000 | 35,000 | 20,000 |
| Ficol 400 or | 200,000 | — | — |
| Sea Plaque agarose (LMT) | 8,000 | — | — |
| Litex HSB agarose (HMT) | — | 6,000 | 6,000 |

Preparation

Macro- and microelements and organic elements are made up two times concentrated, the pH adjusted to 5.6 with 1 M-NaOH and the solution sterile filtered (0.22 μm pore size) before the addition of an equal volume of two times concentrated, autoclaved agarose or Ficoll solution.

Before the spikes were removed from the ensheathing leaves, the tillers were surface sterilized with an aerosol of 96% ethanol. Anthers from a floret in the middle of the spike were stained with a 2:1 mixture of 4% acetocarmine:1% potassium iodine and examined in the light microscope to confirm the initial staging.

Spikes containing anthers in the mid uninucleate stage were cold pretreated at 4° C. for 28 days in two-compartment Petri dishes (Sterilin 501) as described by HUANG and SUNDERLAND (Temperature-stress pretreatment in barley anther culture. Ann. Bot. 49, 77-88 (1982)).

Anthers surviving the cold pretreatment were removed under a dissecting microscope using fine tipped forceps (Dumoxel No. 5), taking care not to rupture the anthers. This was facilitated by bending the lower innermost awn anteriorly, prior to removing the anthers. The anthers were placed directly on solid medium (Table II) and oriented so that only one loculus was in contact with the medium as described by HUNTER (The effect of anther orientation on the production of microspore-derived embryoids and plants of Hordeum vulgare cv. Sabarlis. Plant Cell rep. 4, 267-268 (1985)). The density of the innoculum was two to three anthers per milliliter of medium.

The medium used (Medium I, Table II) are modified MS media (A revised medium for rapid growth and bioassays with tobacco tissues cultures. Physiol. Plant 15, 473–497 (1962)), as described by FOROUGHI-WEHR et al. (Plant production from cultured anthers of Hordeum vulgare L. Z. Pflanzenzuchtg. 77, 198–204 (1976)), solidified with 0.8% Sea Plaque Agarose (FMC Bioproducts, Maine) for induction of culture on solid medium or containing 20% Ficoll 400 (Pharmacia) for induction on liquid medium. For regeneration 0.6% Litex HBS agarose (Litex, Denmark) was used (Media II and III). The media was prepared as described in the legend to Table II. Nutritional elements were from Merck, organic elements from Sigma and Fe-EDTA from Fluka. In addition to the media listed in Table II, culture experiments were performed on media in which the concentration of ammonium nitrate, glutamine and asparagine were changed as described in sections 3.1 and 3.2.

The culture container, a 50 mm Petri dish, 18 mm high (Sterilin 124), was sealed with Nescofilm (Nippon Shoji Kaisha, Osaka, Japan) and placed inside a 140 mm Petri dish together with an unsealed 50 mm Petri dish containing water. The large Petri dish was finally sealed with Nescofilm as described by LYNE et al (Embryoid and plant production from cultured barley anthers. In: Plant Tissue Culture and its Agricultural Application. University of Nottingham. pp. 405–411. Eds: L. A. Withers and P. G. Alderson. Butterworth, pub., Guildford (1984)).

The cultures were incubated at 25° C. in the dark. Calli or embryoids larger than 2 mm were transferred to medium II, at a density of 16 structures per 10 ml of medium per Petri dish (Sterilin 124), (20 cm$^3$ air above the culture) and were incubated in the dark for 5 days at 25° C. Thereafter, the cultures were maintained at 23° C., 10 h light, (60 $\mu$E·m$^2$·s$^{-1}$ Philips cold white) until greening of the coleoptile was observed.

The green plantlets were then transferred to medium III for further development. Each 60 ml containers (Sterilin 125 AP) holding one green plantlet and 25 ml medium, at 23° C., 10 h light, (60 $\mu$E·m$^2$·s$^{-1}$ Philips cold white).

When several shoots and roots had developed, the plants were vernalized while still in the containers for root development (4° C., 10 h light, 20 $\mu$E·m$^2$·s$^{-1}$ Philips warm white). After 6 weeks the plants, together with the surrounding solid medium, were potted in K-soil and transferred to a greenhouse.

REFERENCES

Foroughi-Wehr, B., G. Mix, H. Gaul & H. M. Wilson. Plant production from cultured anthers of Hordeum vulgare L. Z. Pflanzenzuchtg. 77, 198–204 (1976).

Huang B. & N. Sunderland. Temperature-stress pretreatment in barley anther culture. Ann. Bot. 49, 77–88 (1982).

Hunter C. P. The effect of anther orientation on the production of microspore-derived embryoids and plants of Hordeum vulgare cv. Sabarlis. Plant Cell Rep. 4, 267–268 (1985).

Kao K. N. & D. C. Horn. Induction of pollenplant formation in barley anther culture. International Symposium on Genetic Manipulation in Crops. October 22–26, Beijing, China (1984).

Murashige T. & F. Skoog. A revised medium for rapid growth and bioassays with tobacco tissue cultures. Physiol. Plant 15, 473–497 (1962).

Shed microspore culture. The leaf sheaths with enclosed spikes were surface sterilized by spraying with 70% ethanol. Anthers from fresh spikes were cultured in 5 cm diameter petri dishes containing sterile 0.3M mannitol at a density of 20 anthers per ml of mannitol. A total of 240 anthers were used in this experiment. The Petri plates were sealed with parafilm covered with foil and placed in an incubator at 25° to 28° C.

After 3 days, the mannitol solution containing the microspores shed from the 240 anthers was collected. A number of shed microspores adhered to the petri plates; therefore the plates were gently shaken to get the microspores into the mannitol solution and if needed, extra mannitol was used for rinsing. To prevent unnecessary loss of microspores in pipettes and centrifuge tubes, the microspore-mannitol suspension from different plates was pooled before centrifugation at 500 r.p.m. for 5 minutes. The mannitol was discarded and the microspores were resuspended in 0.6 ml of ovary conditioned (Kohler and Wenzel, 1985) liquid FHG medium (Hunter 1988) containing 1 mg/l IAA and 0.2 mg/l kinetin. All liquid media were filter (Nalgene) sterilized, and ovary-conditioning was with Igri cultivar. FHG medium is the same as Olsen's (1987) anther culture medium except for the replacement of sucrose with maltose (6.2%) and the absence of Ficoll 400 (see Kasha et al. 1989). Approximately 0.2 ml of the suspension ($1.8 \times 10^5$ microspores) was placed in droplet form on top of 3 mm of solidified (0.8% Sea Plaque agarose) FHG medium. A total of three replicates were set up and the plates were wrapped in parafilm, incubated in the dark at 25° C. for 21 to 28 days. Observations on the development of microspores were made routinely with an inverted microscope (Zeiss). If the plates were drying out, one or two (0.5 ml) drops of fresh FHG liquid medium were added.

Regeneration of plantlets. Between 21 to 28 days after culture initiation, the foil was removed and the cultures were transferred to an incubator (22° C.) with low light (30–40 $\mu$E/m$^2$/sec). Embryos and calli that were 1.5 mm or larger in diameter were removed weekly and transferred to the regeneration medium (FHG solidified with 0.8% Sea Plaque agarose). This permitted further development of the smaller structures in the original plates. Once plantlets reached 2 to 4 cm in height they were transferred to vials or flasks with a solidified (0.8% agar) hormone-free MS medium (Murashige and Skoog, 1962) containing 2% sucrose as the sugar source. Plants were later transferred to small pots containing a mixture of peat moss and soil, placed in a growth room and covered for a week with clear plastic cups to maintain high humidity.

REFERENCES

Kohler F. & G. Wenzel. J. Plant Physiol., 121, 181–191 (1985).

Hunter C. P. Ph.D. Thesis. Plant regeneration from microspores of barley, Hordeum Valgare. Wye College, University of London, (1988).

Kasha K. J., A. Ziouddin & U. H. Cho. XIX Stadler Genetics Symp., Missouri, pp 213–236 (1989).

Olsen L. Carlsberg Res. Comm., 52, 393–404 (1987).

Murashige T. & F. Skoog. Physiol. Plant., 15, 473–497 (1962).

A further preferred embodiment includes the use of nurse cells.

Hereafter the present invention is described by referring to the examples but is not deemed to be limited thereto.

EXAMPLE 1

After barley cv. Dissa was seeded, the barley was grown at 12° C. for 16 hours in the light and at 10° C. for 8 hours in the dark to collect the anthers of mid uninucleate stage microspores. The anthers were inoculated on modified MS+Ficol medium. After incubation at 25° C. for 2 weeks, the anthers were opened with tweezers and a spatula to scrape the microspore cells out into DNA solution. After 10 to 20 anthers were taken in 1 ml of the solution, callus and deblis were removed through a nylon mesh of 96 μmØ. By centrifugation (1000 rpm×5 minutes), the solution was concentrated to 20 to 100 μl and recovered. The resulting concentrate was made a sample for processing with a laser pulse. The DNA solution used was composed of Okada solution+15% mannitol+10 μg/ml of pBI221 [marketed by Toyo Spinning Co., Ltd.], 10 μg/ml of pSBG102 (Hm$^r$) [β-glucuronidase structural gene of the aforesaid pBI221 surrounded by BamHI, SstI site is substituted with hygromycin B phosphotransferase structural gene [Gene, 25, 179 (1983)]]+50 μg/ml of Calf Thymus DNA.

A drop of the DNA solution was placed on a Petri dish. In order to avoid drying, a 1% agarose piece of 5 mm square was put thereon. The Petri dish was covered and wounded with a film, which was set in Hitachi Laser Cell Processor.

The sample includes microspore cells, developing single cells and cell mass which began to cause division. The developing single cells which was cytoplasm-rich was chosen and pierced by a laser pulse with an energy of 0.5 V.

After the processing, the sample was diluted in 100 to 200 μl of aMS liquid medium and subjected to stationary culture at 25° C. Two weeks after, an equal volume of the medium (containing hygromycin B) was added. With respect to callus grown to have a diameter of several milimeters, transduction of GUS enzyme was examined. As the result, GUS activity was noted in a ratio of about 1/16.

Hereafter the method for assaying GUS activity is shown.

---

GUS Assay:
Composition of staining solution for gus aassay

X-glu solution (5-bromo-4-chloro-3-indolyl-
β-D-glucuronic acid) storage solvent
[20 mg/l X-glue DMF]
5 mg X-glu in deoxynized DMF (dimethyl-
formamide)
↓
solute in 5 ml of 50 mM K.P. buffer
(potassium phosphate buffer) [pH 7.0, final
concentration of 1 mg/ml]
GUS lysis buffer
50 mM K.P. buffer pH 7.0 + 10 mM EDTA + 0.1%
Triton X 100 + 0.1% Sarkosyl + 10 mM
2-Mercaptoethanol

---

Preparation of cell

When a small colony or the surface of tissue is stained, it may be impregnated with the solution as it is. The colony having a diameter of 100 μm was stained but it is questionable if substrate was incorporated in the plant.

Where the reaction is carried out quantitatively or accurately, a small amount of gus lysis buffer is added to the tissue, the mixture is mushed and substrate is added thereto. In the case of 1 mm calluss, it is sufficient to use 20 μl of gus lysis buffer and 100 μl of X-glu solution.

EXAMPLE 2

After barley cv. Igri was seeded, the barley was grown at 12° C. for 16 hours in the light and at 10° C. for 8 hours in the dark to get the anthers included microspores of mid-uninucleate stage. The anther were inoculated on modified MS+Ficol medium. After incubation at 25° C. for 2 weeks, the anthers were opened with tweezers and a spatula to scrape the pollen cells out into DNA solution. After 10 to 20 anthers were taken in 1 ml of the solution, callus and contaminants were removed through a nylon mesh of 96 μmØ. By centrifugation (1000 rpm×5 minutes), the solution was concentrated to 20 to 100 μl and recovered. The resulting concentrate was made a sample for processing with a laser pulse. The DNA solution used was composed of Okada solution+15% mannitol+10 μg/ml of pBI221 [marketed by Toyo Spinning Co., Ltd.], 10 μg/ml of pSBG102 (hm$^r$) [β-glucuronidase structural gene of the aforesaid pBI221 surrounded by BamHI, SstI site is substituted with hygromycin B phosphotransferase structural gene [Gene, 25, 179 (1983)]]+50 μg/ml of Calf Thymus DNA.

A drop of the DNA solution was placed on a Petri dish. In order to avoid drying, a 1% agarose piece of 5 mm square was put thereon. The Petri dish was covered and wounded with a film, which was set in Hitachi Laser Cell Processor. The sample was treated automatically with an energy of 0.5 V.

After the processing, the sample was diluted in 500 μl of modified MS liquid medium and subjected to stationary culture at 25° C. Two weeks after, an equal volume of the hygromycin-selection medium (20 mg/l hygromycin B) was added. With respect to callus grown to have a diameter of several milimeters, transduction of GUS enzyme or hygromycin resistance was examined. As the result, GUS activity was noted in a ratio of about 1/2000.

Regeneration of plant Regeneration of transgenic barley

Leaf primordium corresponding to cotyledon was transplanted to rooting medium and cultured under the same conditions to promote development of the root and growth of shoot. A complete plant was regenerated in about a month. From the living leaves, nuclear DNA was isolated by the CTAB method (Plant Molecular Biology Reporter, 7:2, 116, 1989).

The details of the method are described hereunder.

Solution required

The DNA extraction buffer consisted of 0.14M sorbitol, 0.22M Tris-HCl, 0.022M EDTA, 0.8M NaCl, 0.8% (W/V) hexadecyltrimethylammonium bromide (CTAB), and 1% N-laurylsarcosine. The PCR reaction mixture contained 50 mM KCl, 10 mM Tris-HCl (pH 8.5 at 25° C.), 2.5 mM MgCl$_2$, each primer at μM, each dNTP (dATP, dGTP, dCTP, and TTP) at 200 μM, gelatin at 200 μM/ml, and Taq DNA polymerase at 20 units/ml (Saiki et al., 1988).

Isolation of plant DNA

We developed a miniscreen technique for plant DNA which is suitable for the rapid isolation of tomato and tobacco DNA. The method is a modification of the CTAB method (Bernatzky and Tanksley, 1986) and the viral sap extractor technique of Clarke et al. (1989).

A small leaf (50 to 500 mg of tissue) was macerated in 100 µl of extraction buffer in microfuge tube with a Kontes pestle, and the extract eluted into a 1.5 ml microfuge tube containing 300 µl of chloroform; enough extraction buffer was used to fill the microfuge tube. The tube was closed, inverted several times, and immediately placed in a 65° C. heating block. After heating for 5 to 30 minutes (while the other samples were processed), the mixture was transferred to a fresh microfuge tube, inverted a number of times to form an emulsion, and centrifuged for 5 min at full speed in an Eppendorf centrifuge. We found it necessary to change tubes after heating to avoid breakage of the tubes during centrifugation. The upper aqueous phase was transferred to a 1.5-ml microfuge tube containing 600 µl of isopropanol, the tube was inverted several times, and centrifuged for 5 min. The pellet was washed with 70% ethanol, dried in vacuum, and resuspended in 50 to 200 µl of TE.

The chloroform extraction and isopropanol precipitation were performed as described but scaled down in volume accordingly. We have successfully amplified single-copy genomic sequences from DNA isolated from 5 mg of leaf tissue.

Starting with 50 to 500 mg of leaf tissue, our miniscreen technique typically yields from 10 to 100 µg of DNA. The quality of DNA was superior if extracted from healthy young plants and was suitable for Southern analysis of single-copy sequences as illustrated in FIG. 5 on page 124 of Lassner et al (Plant Molecular Biology Reporter, vol. 7(2), 1989). DNA isolated from older yellowing tissue tended to be more degraded, but was generally of adequate quality for PCR analysis.

REFERENCES

Bernatzky R. & S. D. Tanksley. Genetics of actin-related sequences in tomato. Theor. Appl. Genet. 72, 314–321 (1986).

Clarke B. C., L. B. Moran and R. Appel. DNA analyses in wheat breeding. Genome, in press (1989).

Using 20 mers of the structural gene portion of marker gene as primers, it was attempted to conduct PCR (Science, 239:487, (1988). That is, DNA synthesis was performed with 1 µg genomic DNA, a pair of 1 µm primers, 20 µm NTP's (dATP, dCTP, dGTP, dTTP) and 2 units of Taq polymerase in a reaction buffer consisting of 50 mM KCl, 10 mM Tris-HCl (pH 8.4), 2.5 mM $MgCl_2$, and 200 µg/ml gelatin. The thermal conditions employed for 30 cycles of PCR were 37° C. for 2 min.—72° C. for 3 min.—94° C. for 1 min. The results were observed by means of agarose gel electrophoresis whereby DNAs equivalent to the respective genes were synthesized. From this, the presence of foreign genes in nuclear genome was confirmed.

By applying the present invention, the culture cells of Gramineae can be transformed. According to the present invention, it is unnecessary to prepare protoplast and therefore, time and operations for transformation can be greatly reduced. Since haploid cells are transformed, the character transduced is conveyed without separating at a later generation. In addition, difficulties in experiments between species and cultivars are minimized so that it is easy to apply the present invention to practical species. According to the present invention, large pores can be formed as compared to the electroporation method so that DNA or substances having a large molecular weight can be introduced.

What is claimed is:

1. A method for preparing a transformed plant of barley which comprises culturing an anther of barley in a callus induction medium and, at a stage of initial microspores or globular cell clusters prior to the microspore-wall breakage during the microspore culture, transducing a genetic substance into said microspore cell through a pore formed by a laser pulse thereby expressing said genetic substance in said microspore, said plant, or both said microspore and said plant.

2. A method for preparing a transformed plant of barley which comprises culturing an anther of barley in a callus induction medium and, at a stage of initial microspores or globular cell clusters prior to the microspore-wall breakage during the microspore culture, transducing a genetic substance into said microspore cell through a pore formed by a laser pulse.

3. A method for preparing a transformed plant of barley, comprising culturing an anther of barley in a callus induction medium to produce a microspore cell or globular cell clusters;

4. The method of claim 1, 2 or 3, wherein said pore formed by said laser pulse has a diameter of 5–500 nanometers.

5. The method of claim 1, 2 or 3, wherein said laser pulser is applied for a time period in the range of 5 to 50 nanoseconds.

6. The method of claim 5, wherein said laser pulse has a pulse energy in the range of 0.1 to 10 µJ.

7. The method of claim 1, 2, or 3, wherein transducing is conducted for a period of time in the range of 5 seconds to 2 hours.

8. The method of claim 7, wherein said transducing is conducted by incubating said microspore cells with said genetic substance at a temperature of from 0° to 28°C.

* * * * *